Dec. 12, 1972 C. G. KLEHM Plant Pat. 3,271
PEONY PLANT
Filed Feb. 22, 1971
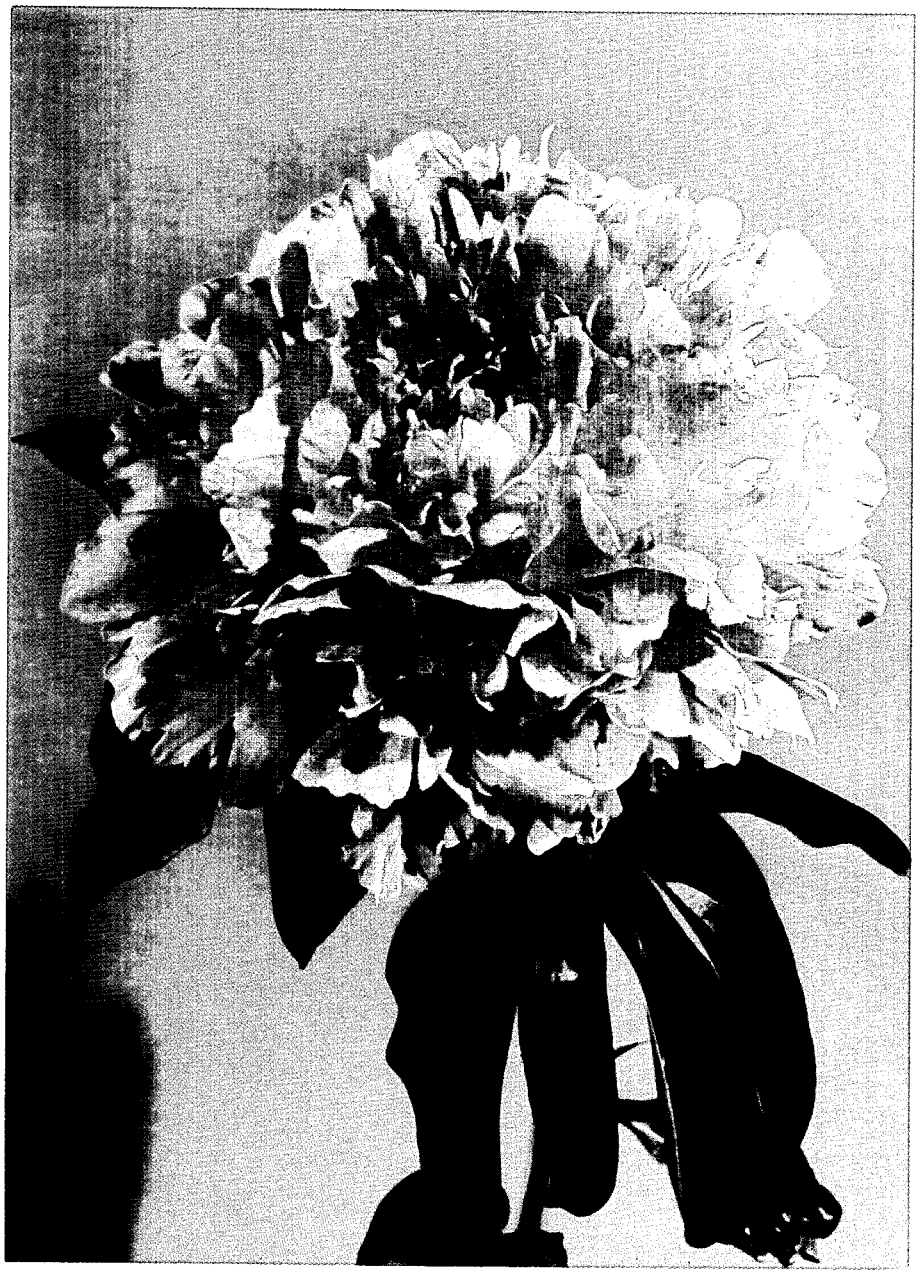
Inventor.
Carl G. Klehm
By: Robb & Robb
Attorneys.

United States Patent Office

Plant Pat. 3,271
Patented Dec. 12, 1972

3,271
PEONY PLANT

Carl G. Klehm, 2 E. Algonquin Road, Arlington Heights, Ill. 60005

Filed Feb. 22, 1971, Ser. No. 117,846
Int. Cl. A01h *5/00*
U.S. Cl. Plt.—68 1 Claim

The present invention relates to a new and distinct variety of peony plant of the species botanically known as *Paeonia lactiflora,* which was originated by me by crossing an unnamed and unpatented "bull" type peony seedling, identified in my breeding records as No. 71D, with the peony variety known as "Mons. Jules Elie" (unpatented), the unnamed seedling being the male parent and "Mons. Jules Elie" being the female parent.

My new variety resulted from an extensive and prolonged program of breeding and testing conducted by me in an effort to produce new and improved or unique peony varieties, and was selected as one of many outstanding varieties resulting from this breeding program because of its unique combination of the following principal characteristics which distinguish the new variety from its parents, as well as from all other peony varieties of which I am aware:

(1) An extremely vigorous plant habit;
(2) Strong, stout, tall and straight stems;
(3) Very large flowers of fully double-rose type form;
(4) A distinctive and attractive blend of cherry red, rose red and vivid rose pink flower colors, with a slight moon silver petal edging; and
(5) Especial suitability for cut-flower uses.

Asexual reproduction of my new peony variety by root division, as performed by me in my nursery located at Arlington Heights, Ill., shows that the foregoing characteristics and distinctions come true to form and are established and transmitted through succeeding propagations.

The accompanying drawing shows typical specimens of the vegetative growth and flowers of my new variety, as depicted in color as nearly true as it is reasonably possible to make the same in a color illustration of this character.

The following is a detailed description of the new variety, with color terminology in accordance with the Horticultural Colour Chart (1966 edition), published by The Royal Horticultural Society, of London, England, as based on specimens grown and observed by me at Arlington Heights and Barrington, Illinois:

Breeding: Seedling.
*Seed parent*—"Mons. Jules Elie."
*Pollen parent*—An unnamed seedling identified as No. 71D.

Propagation: Holds its distinguishing characteristics through succeeding propagations by root division.

Flower

Blooming habit: Annual.
Blooming season: Mid-season.
Bud:
*Size.*—Large.
*Form.*—Rippled, but relatively round.
*Color.*—Rose bengal, Fan Z, Plate 57B′.
*Sepals.*—Rippled edges. Color—Green.
*Calyx.*—Polysepalous.
*Opening.*—Opens easily, with occasional calyx splitting, but a dependable yearly performer.

Bloom:
*Size.*—Extremely large (from about 8 inches to 8½ inches).
*Borne.*—Singly; one main bud per stem, with 3 or 4 auxiliary buds.
*Stems.*—Strong; tall (from about 32 inches to 38 inches).
Form.—Double-rose type, with one row of guard petals.
*Petalage.*—Double.
*Color.*—A blend of cherry red, rose red and vivid rose pink, with slight moon silver petal edging, but mainly Fan 1, Plate 50 A′.
*Variegations.*—None.
*Discolorations.*—None, but seasonal solar intensity affects the amount of silver petal edging.

Petals:
*Texture.*—Thick.
*Appearance.*—Dense; shiny.
*Form.*—Recurved.
*Arrangement.*—Imbricated.
*Persistence.*—Excellent.
*Fragrance.*—Strong typical peony scent.
*Lasting qualities.*—Excellent.

*Reproductive organs*

Organs: None.
Fruit: None.

*Plant*

Form: Bush.
Growth: Tall; robust; vigorous; healthy.
Foliage:
*Leaflets.*—5 or 6 in number.
*Size.*—Large.
*Quantity.*—Average.
*Color.*—Dark green, Fan 3, Plate 136 B′.
*Shape.*—Elliptically acute.
*Texture.*—Smooth.
*Edge.*—Smooth.
*Serrations.*—None.
*Leaf stem.*—Thick.
*Stipules.*—None.
*Disease resistance.*—Resistant to leaf blotch and other bacterial peony diseases, as determined by comparison with other varieties for many years as grown at Arlington Heights and Barrington, Ill.

*General observations*

The new variety is principally outstanding for its huge, bold flowers which are borne on tall, strong and straight stems and which are of an attractive vivid red color.

I claim:

1. A new and distinct variety of peony plant of the species botanically known as *Paeonia lactiflora,* substantially as herein shown and described, characterized particularly as to novelty by the unique combination of an extremely vigorous plant habit, strong, stout, tall and straight stems, very large flowers of fully double-rose type form, a distinctive and attractive blend of cherry red, rose red and vivid rose pink flower colors, with a slight moon silver petal edging, and especial suitability for cut-flower uses.

No references cited.

ROBERT E. BAGWILL, Primary Examiner